United States Patent [19]  [11] 4,048,185
Pintschovius et al.  [45] Sept. 13, 1977

[54] BENZOXAZOLE DERIVATIVES, PROCESS FOR THEIR PREPARATION AND THEIR USE AS OPTICAL BRIGHTENERS

[75] Inventors: Ulrich Pintschovius, Hattersheim (Main); Erich Schinzel, Hofheim, Taunus; Günter Rösch, Altenhain, Taunus, all of Germany

[73] Assignee: Hoechst Atiengesellschaft, Frankfurt am Main, Germany

[21] Appl. No.: 693,941

[22] Filed: June 8, 1976

[30] Foreign Application Priority Data

June 12, 1975 Germany .............................. 2526230

[51] Int. Cl.[2] ........................................... C07D 263/54
[52] U.S. Cl. ........................ 260/307 D; 260/45.7 PH; 260/45.8 NZ; 260/471 R; 260/471 A; 260/519; 252/301.28; 560/43; 560/44
[58] Field of Search .................................... 260/307 D

[56] References Cited

U.S. PATENT DOCUMENTS

| | | | |
|---|---|---|---|
| 3,709,896 | 1/1973 | Frischkorn et al. | 260/307 D |
| 3,755,343 | 8/1973 | Anliker et al. | 260/307 D |
| 3,872,094 | 3/1975 | Meyer | 260/307 D |

Primary Examiner—Raymond V. Rush
Attorney, Agent, or Firm—Connolly and Hutz

[57] ABSTRACT

Compounds of the general formula I

I,

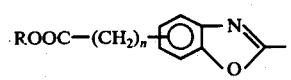

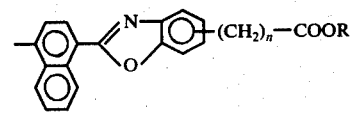

in which R represents hydrogen or a lower alkyl radical which may be further substituted, $n$ is an integer of from 1 to 4, and which may contain further non-chromophoric substituents. They are prepared by reaction of the dichloride of naphthalene-1,4-dicarboxylic acid with an o-aminophenol and subsequent ring closure. These compounds can be used as optical brighteners.

2 Claims, No Drawings

BENZOXAZOLE DERIVATIVES, PROCESS FOR THEIR PREPARATION AND THEIR USE AS OPTICAL BRIGHTENERS

The present invention relates to benzoxazole derivatives, to a process for their preparation and their use as optical brighteners.

It has already been known to use 1,4-bis-[carbalkoxybenzoxazolyl]-naphthalenes as optical brighteners (German Offenlegungsschrift No. 1745 622).

The present invention provides 1,4-bis-[carboxylalkyl-benzoxazolyl]-naphthalene derivatives which are colorless or slightly yellow, which have in solution a more or less pronounced blue to greenish blue fluorescence, and which correspond to the general formula I

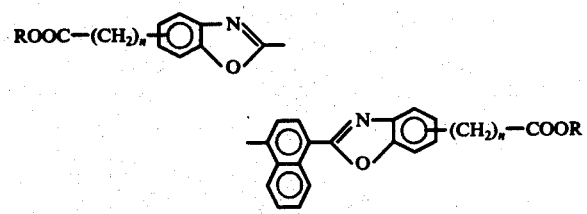

in which R represents a lower, optionally further substituted alkyl radical or a hydrogen atom, n is an interger of from 1 to 4, and which may contain further non-chromophoric substituents.

As non-chromophoric substituents there may be mentioned first of all preferably lower alkyl groups, preferably lower alkenyl groups, preferably lower alkoxy groups, aryl radicals, preferably phenyl radicals, aralkyl groups which are preferably derived from lower alkylene and phenyl radicals, such as benzyl and phenylethyl groups, acyl groups, optionally functionally modified carboxy groups, acylamino or sulfonyl groups, as well as halogen atoms. Two lower alkyl radicals may also form together a fused cycloalkyl or phenyl ring.

Preferred compounds of the invention are those which correspond to the general formula II

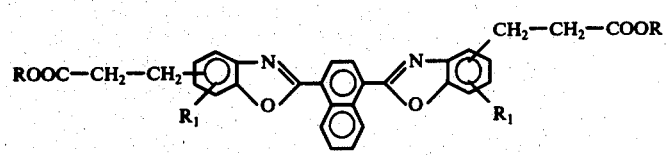

in which R and $R_1$ represent a lower alkyl radical which may be branched, or a hydrogen atom.

The compounds of the invention can be synthesized according to the processes of preparation specified in the following, R and n having the meanings given under I above:

The dichloride of the naphthalene-1,4-dicarboxylic acid is condensed with 2 moles of o-amino-phenols of the general formula III

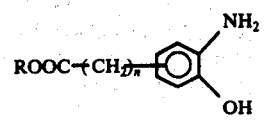

preferably in the presence of an acid-binding agent, and the bisacylamino compounds obtained of the general formula IV

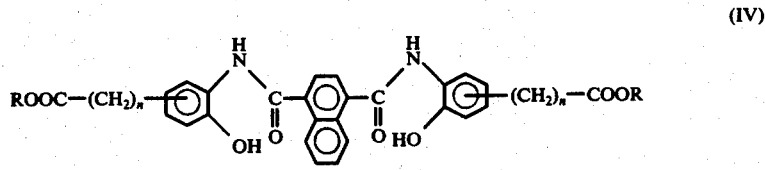

are cyclisized in an inert gas atmosphere in high-boiling solvents, preferably trichlorobenzene or mixtures thereof, at an internal temperature of from 200° to 250° C, in the presence of catalysts, such as zinc chloride or p-toluene-sulfonic acid, to give the compounds (I) of the invention.

As o-aminophenols of the formula IV there may be used, for example:
β-(3-Amino-4-oxy-phenyl)-propionic acid -methylester
β-(3-Amino-4-oxy-phenyl)-propionic acid -ethylester
β-(3-Amino-4-oxy-phenyl)-propionic acid
β-(2-methyl-5-amino-4-oxy-phenyl)-propionic acid-methylester
β-(2-methyl-5-amino-4-oxy-phenyl)-propionic acid-butylester
3-amino-4-oxy-phenyl-acetic acid-ethylester
3-amino-4-oxy-phenyl-acetic acid-butylester
3-amino-4-oxy-phenyl-acetic acid
6-chloro-3-amino-4-oxy-phenyl-acetic acid-methylester
γ-(3-amino-4-oxy-phenyl)-butyric acid-methylester
γ-(3-amino-4-oxy-phenyl)-butyric acid-ethylester
δ-(3-amino-4-oxy-phenyl)-valeric acid-methylester.

A further process for the preparation of the compounds of the formula I comprises converting the corresponding cyano compounds with alkanols and hydrogen chloride into the compounds of the formula I which contain carbalkoxyalkyl groups. The reaction products obtained in the above-mentioned processes may be subjected to further known transformation reactions, for example, halogenation, chloromethylation, sulfochlorination processes, and also to those transformation reactions which use chlorosulfonated or carboxyl-containing molecules as starting compounds and yield compounds having functionally modified sulfo or carboxy groups, and/or to the conversion reactions of these groups into other groups of this kind or into the free acids, for example, by transesterification or hydrolysis.

In this way the compounds can be prepared for example by hydrolyzing the methyl ester described in Example 1 and by optional re-esterification of the obtained free dicarboxylic acid with 2-ethoxyethanol, ethanol, propanol, butanol or any other alcohol such as chloro- or hydroxy-substituted alcohols with 1 to 4 carbon atoms.

According to the preparation processes described above and by the transformation of the condensation products obtained, the following compounds can be prepared, for example:

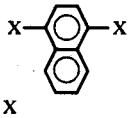

| | X |
|---|---|
| 101 | $CH_2-CH_2-COOCH_3$ |
| 102 | $CH_2-CH_2-COOC_2H_5$ |
| 103 | $CH_2-CH_2-COO-(CH_2)_3-CH_3$ |
| 104 | $CH_2-CH_2-COO-CH_2-CH_2-O-CH_3$ |
| 105 | $CH_2-CH_2-COO-CH_2-CH_2-OH$ |
| 106 | $CH_2-CH_2-COO-CH_2-CH_2Cl$ |
| 107 | $CH_2-CH_2-COO-CH_2-COOCH_3$ |
| 108 | $CH_2-CH_2-COOH$ |
| 109 | $CH_2-CH_2-COOC_2H_5$, $CH_3$ |
| 110 | $CH_2-COOH$ |
| 111 | $CH_2-COOCH_3$ |
| 112 | $CH_2-COOC_2H_5$ |
| 113 | $CH_2-COO-CH_2-CH_2-O-O$ |
| 114 | $CH_2-CH_2-CH_2-COOH$ |
| 115 | $CH_2-CH_2-CH_2-COOCH_3$ |

-continued

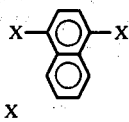

| 116 | $CH_2-CH_2-CH_2-CH_2-COO$ |
| 117 | $CH_2-CH-COOCH_3$, $CH_3$ |
| 118 | $CH_2-COOC_2H_5$, $CH_3$ |

Due to their excellent fluorescent properties, the compounds of the invention can be used in a wide field of application. In particular they may be used for the optical brightening of various natural and synthetic organic materials. By this term there are to be understood also those organic materials which may be used for the processing of mineral substances, for example of inorganic pigments.

As substrates which can be optically brightened there are mentioned the following materials, for example: Coating materials, synthetic fibers, such as those made of acetyl cellulose, polyamides, plyolefins, polyvinylchloride, polyvinylidene chloride and polyacrylonitrile, as well as foils, films, ribbons and shaped articles made of these materials.

The compunds of the invention which are insoluble in water may be used dissolved in organic solvents or in the form of an aqueous dispersion, advantageously while using a dispersing agent. As dispersing agents there may be mentioned, for example, soaps, polyglycolethers which are derived from fatty alcohols, fatty amines or alkyl phenols, waste liquors of cellulose sulfite or condensation products of optionally alkylated naphthalene-sulfonic acids with formaldehyde.

The brightening of the fiber material with the aqueous or possibly organic brightening bath may be carried out either according to the batchwise exhaustion method at a temperature in the range of preferably from about 20° to 150° C, or under thermosoling conditions, in which process the textile material is impregnated or sprayed, for example, with the brightening solution and/or dispersion and is then squeezed off, for example, between rollers, to a residual brightening solution and/or dispersion content of from about 50 to about 120%. Subsequently the textile material is subjected, for about 10 to about 300 seconds, to a temperature treatment, preferably with dry heat, at a temperature of from about 120° to 240° C. This thermosoling process may also be combined with other finishing operations, for example, the treatment with synthetic resin to obtain easycare properties, in which process the material is condensed, optionally after the impregnation and drying at a temperature of from 100° to 150° C, for 5 to 20 minutes at a temperature of from 150° to 200° C, for the purpose of cross-linking.

The compounds of the general formula (I) may also be added to detergents, which may contain the common filling and auxiliary agents, such as alkali metal silicates, alkali metal phosphates and/or condensed phosphates, alkali metal borates, alkali metal salts of the carboxy methyl celluloses, foam stabilizers, such as alkanolamides of higher fatty acids or complexing agents, such as soluble salts of ethylene-diamine-tetra-acetic acid or diethylene-triamine-pentaacetic acid, as well as chemical bleaching agents, such as perborates or percarbonates, perborate activators of the polyacetic acid-amide type, which in conjunction with the peroxo compounds lead to the splitting-off of peracetic acid, and disinfectants. Moreover, the compounds of the invention may be added to high-molecular-weight organic materials before and/or during the forming process. Thus, for example, they may be added to the plastics moulding powders, thermoplastic moulding compositions, melts, polymer solutions or dispersions. If fibers, films, foils, ribbons, plates or other shaped articles are being produced, for example, they are dissolved in the spinning solution before spinning. In the case of polyamide-6, polyamide-6,6 or linear polyesters of the polyethylene-glycol-terephthalate type, for example, suitable compounds may be added to the low molecular weight starting materials prior to polycondensation or polymerization.

It is of special importance that the compounds of the invention which are substituted by two carboxy or carboalkoxy groups may be bound to linear polyester molecules and synthetic polyamides by an ester or amide bond, if they are added to these materials under suitable conditions, or are preferably added to their starting compounds. Brighteners incorporated into the substrate by a chemical bond in this manner are distinguished by an extremely high fastness to sublimation and to solvents.

According to the latter process, the compounds of the invention may be used advantageously also in admixture with other brightener molecules to be incorporated, for example, the compounds of the formla V

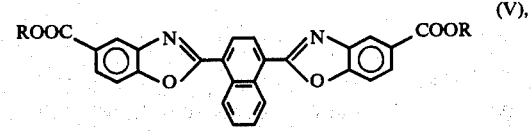

(V), in which R represents the radical of a lower aliphatic alcohol which may be substituted, in particular a methyl, ethyl or β-hydroxyethyl group. In this process an excellent degree of whiteness was obtained which showed a very good fastness to light, sublimation and solvents. By varying the ratio of mixture of suitable compounds of the invention with the compounds (V), the color shade of the optically brightened synthetic fibers may be influenced, and the requirements of the market with regard to the shade of white can thus be met.

The amount of the compounds of the general formula (I) to be used according to the invention, calculated on the material to be brightened optically, may vary within a wide range, depending on the field of application and the desired effect. It can be determined easily by means of simple preliminary tests, and is generally in the range of from about 0.01 to about 2%, preferably from 0.02 to 0.1%.

The following Examples serve to further illustrate the invention. The temperatures are indicated in degrees Celsius; the percentages are parts by weight, unless otherwise stated.

EXAMPLE 1

(Preparation)

17.4 Grams of naphthalene-dicarboxylic acid-(1,4) were heated in 80 ml of chlorobenzene with 22.3 g of thionylchloride for about 5 hours at a temperature of from 100° to 110° C. 40 Milliliters of toluene were distilled off in the nitrogen current at 105° to 110° C, and the parts by volume which had passed over were replaced by fresh toluene. The acid chloride solution thus obtained was introduced, at a temperature of from 70° to 75° C, within 15 minutes, into a mixture of 33.0 g of β-[3-amino-4-oxyphenyl]-propionic acid-methylester and 20.3 g of dimethylaniline in 200 ml of toluene, the mixture was continued to be stirred for 2 hours at the same temperature, and was then allowed to cool, while being stirred. The diamide which precipitated following a steam distillation was separated, was washed with toluene and methanol and dried. 45.0 Grams of the diamide were obtained, which had a melting point of from 237° to 238° C.

TABLE $$ROOC-CH_2-CH_2-\text{[structure]}-CH_2-CH_2-COOR$$

Absorption measured in dimethylformamide

| No. | R | $R_1$ | melting point | $\lambda_{max}$ [nm] | $\epsilon \cdot 10^{-3}$ |
|-----|---|-------|---------------|----------------------|--------------------------|
| 201 | $CH_3$ | H | 175 to 176° | 380 | 36.5 |
| 202 | $C_2H_5$ | H | 130 to 131° | 377 | 36.6 |
| 203 | $CH_2-CH_2-O-C_2H_5$ | H | 107 to 108° | 378 | 36.6 |
| 204 | H | H | 261 to 262° | 378 | 34.7 |
| 205 | $CH_3$ | $CH_3$ | 202 to 203.5° | 386 | 40.1 |

45 Parts by weight of the diamide obtained were heated in 230 ml of 1,2,4-trichlorobenzene with the addition of 0.4 g of p-toluenesulfonic acid in a slight nitrogen current for 2 hours at a temperature of about 210° C (internal temperature). About 165 milliliters of trichlorobenzene were distilled off, and at 100° C, 250 ml of ethanol were added. The mixture was cooled to room temperature, and the separated 1,4-bis[5'-(β-carbomethoxyethyl)-benzoxazolyl-(2')]-naphthalene (compound 201) was filtered off with suction. The product was washed with ethanol and dried. 36.4 Parts by weight of the above-mentioned compound were obtained, which had a melting point of from 167° to 171° C. A product which had been recrystallized several times from DMF or toluene had a melting point in the range of from 175° to 176° C (yellow crystals).

EXAMPLE 2

26.7 Grams of the dimethylester (compound 201; cf. also Example 1) were dissolved in 50 ml of ethyleneglycol, while being heated to about 190° C. To this solution, 5.0 g of sodium hydroxide solution were added, and the whole was heated again for 10 minutes. Then the mixture was diluted, while being cooled with water, and was then acidified with hydrochloric acid. By way of suction-filtration, washing with water and drying, 25.1 g (99%) of a yellow powder of the dicarboxylic acid (204) were obtained, which had a melting point of from 261° to 262° C (which could be recrystallized from glacial acetic acid or o-dichlorobenzene).

EXAMPLE 3

10.0 Grams of the dicarboxylic acid prepared in the above Example (204) were refluxed with 800 ml of absolute ethanol and 4 ml of sulfuric acid of 100% strength for 7 hours. After the mixture had been cooled and had been allowed to stand overnight, and after suction-filtration, washing with water and drying, 9.5 g (86% of the theory) of diethylester (202) could be isolated, which could be recrystallized from methylglycol. The melting point was in a range of from 130° to 131° C.

EXAMPLE 4

26.7 Grams of dimethylester (compound 201; cf. Example 1) were heated, together with 100 ml of anhydrous ethylglycol (glycolmonoethylether) and 12 millimoles of the sodium compound of the ethylglycol, for 120 minutes at a temperature in the range of from 125° to 135° C (internal temperature), in which process part of the solvent distilled over slowly. Finally, almost the total amount of solvent was distilled off at the water jet vacuum pump, and water was added. The transesterification product was filtered off with suction, was washed with water, dried and was thereafter purified by recrystallization from cyclohexane. 26 Grams of a greenish-yellow crystal powder (203) were obtained, which had a melting point of from 107° to 108° C.

EXAMPLE 5

11.5 Grams of naphthalene-1,4-dicarboxylic acid (94% strength) were converted in 70 ml of toluene with 8.5 ml of thionylchloride into the chloride. At a temperature of from 70° to 80° C, the toluene solution of the acid chloride which had been freed from the excess thionyl chloride by distillation in vacuo was introduced into a suspension of 22.0 g of $\beta$-[3-amino-4-oxy-6-methyl-phenyl]-propionic acid-methylester (melting point of from 100° to 102° C, obtained by catalytic reduction of the nitro compound having a melting point of from 88° to 89° C) in 100 ml of dioxane and 9.0 g of pyridine, which suspension was stirred under a nitrogen atmosphere, and the whole was heated for another 5 hours at 75° C. The total reaction mixture was distilled with steam, the precipitate was filtered off with suction at 30° C, after hydrochloric acid had been added, was then washed with water and dried.

The acylamino compound thus obtained (16.0 g with a melting point of from 231° to 235° C) was then cyclisized by a heating process for about one hour under a nitrogen atmosphere, in 100 ml of trichlorobenzene (-mixture) in the presence of 0.3 g of zinc chloride as catalyst. The principal amount of the trichlorobenzene was distilled off in vacuo; the residue was mixed with 100 ml of methanol, while being still warm. The crystals were filtered off with suction at 15° C, then washed with methanol and dried. 14.5 Grams of compound 205 were obtained in the form of an olive-greenish crystal powder. The raw product could be purified by way of recrystallization from toluene or DMF, to give a yellow crystal powder having a melting point of from 202° to 203.5° C.

EXAMPLE 6

12 Parts by weight of dimethylterephthalate, 8 parts by weight of ethylene-glycol and 0.025% of the brightener compound No. 201 (cf. Table shown above) were melted under a nitrogen atmosphere in a stainless stell vessel provided with a stirring device, at a temperature of from 140° to 150° C. After the melt had reached a temperature of 145° C, it was mixed with 0.02 parts of manganese acetate dissolved in one part of glycol. In a temperature range of from 160° to 220° C, the transesterification was carried out within 3 hours under atmospheric pressure, in which process methanol and, towards the end, part of the glycol were distilled off. The bis-($\beta$-hydroxyethyl)-terephthalate obtained was brought to a temperature of 240° C in a condensation vessel made of stainless steel, after 1 part by weight of ethylene-glycol had been added, together with 0.03% of antimony trioxide
0.40% of titanium dioxide
0.031% of triphenylphosphite.

When this temperature had been reached, the pressure in the reaction vessel was slowly reduced to a final vacuum of 0.4 Torr and the temperature was increased at the same time from 240° to 278° C. After 4 hours the polycondensation was finished. The vacuum was eliminated, and in the course of this process the free reaction space above the melt was filled with nitrogen standing under pressure. Subsequently the melt was pressed out by the nitrogen pressure, and was granulated after chilling in water and dried. The product obtained had a softening point of about 260° C and an inner viscosity of about 600. It was spun into threads in common manner according to the melt spinning process, which threads were processed into tubes of knitted fabric.

In this manner a material was obtained, which showed a considerably higher degree of whiteness than was the case without using the brightener compound No. 201 (cf. Table).

In the same manner, good brightening effects could be obtained with the compounds 202, 203, 204 or 205. Similar results were also obtained, if instead of the compounds 201 or 205 alone use was made of their mixtures with the compound of the formula V (R = methyl). With a constant use of brightener compound of 0.025% and an increasing proportion of the compound V, the shade of the material obtained became redder.

EXAMPLE 7

12 parts by weight of dimethylterephthalate and 8 parts by weight of ethylene-glycol were melted under a nitrogen atmosphere in a stainless steel vessel provided with a stirring device at a temperature of from 140° to 150° C. The melt which was heated to 145° C was mixed with 0.02 part of zinc acetate dissolved in 1 part of glycol. In a temperature range of from 160° to 220° C, under atmospheric pressure, the reaction was carried out within 3 hours, in which process methanol and, towards the end, part of the glycol were distilled off.

The bis-($\beta$-hydroxyethyl)-terephthalate was pressed into a condensation vessel made of stainless steel. After 1 part by weight of ethylene-glycol had been added together with
- 0.03% of antimony trioxide
- 0.40% of titanium dioxide
- 0.031% of triphenylphosphite, and
- 0.025% of the brightener compound No. 201, the temperature of the melt was brought to 240° C. When the above-mentioned temperature had been reached, the pressure in the reaction vessel was slowly reduced to a final vacuum of 0.4 Torr., and at the same time the temperature was increased to 278° C. After 4 hours the polycondensation was finished. The vacuum was eliminated, and the space above the melt was filled with nitrogen standing under pressure. Subsequently the melt was pressed out by the nitrogen pressure and was granulated after chilling in water and dried. The product obtained had an inner viscosity of about 600 and a softening point of about 260° C. The granules were spun into threads in common manner according to the melt spinning process, and were processed into tubes of knitted fabric.

The material thus obtained showed a degree of whiteness which was considerably higher than that of the material prepared without using the brightener compound No. 201.

Similarly good results were also obtained by means of mixtures of the brightener compound 201 and compound V (R = lower alkyl, especially methyl). In this connection, an increasing proportion of compound V (at 250 ppm of total brightener compound) cause the color shade to become redder.

EXAMPLE 8

0.03 Part of compound 201 and/or 202 or 203 were homogeneously distributed by stirring in
- 75 parts of polyvinylchloride powder
- 25 parts of dioctylphthalate
- 1.5 parts of barium-cadmium stabilizer
- 2 parts of titanium dioxide, and
- 0.2 part of wax "E" of the Hoechst Corp.

The composition was then plasticized between heated polished steel rollers for 10 minutes at 160° C and was then rolled to give a sheet of a thickness of 0.5 mm.

The foil obtained showed a degree of whiteness which was considerably higher, as compared against that of foils without the addition of compounds 201, 202 or 203.

EXAMPLE 9

1.5 Grams of titanium dioxide and
0.03 g of the compound 201 and/or 202 or 203 were powdered in a regular manner onto
98.5 g of polystyrene granules in a rotating vessel.

The material thus obtained was processed, by means of the injection moulding machine, at a temperature of from 200° to 220° C, into platelets having a thickness of 2 mm.

The platelets thus produced which contained the compound 201, 202 or 203 showed a degree of whiteness which was considerably higher than that of material which had not been brightened.

We claim:

1. A compound of the formula

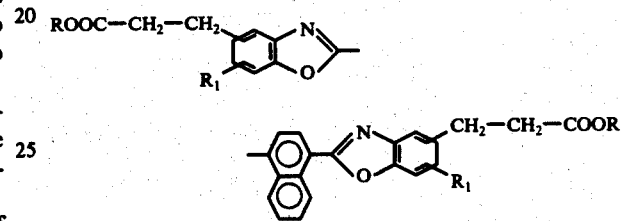

wherein
R is hydrogen, ethoxyethyl, methyl, ethyl, propyl or butyl and
$R_1$ is hydrogen or methyl.

2. A compound of the formula

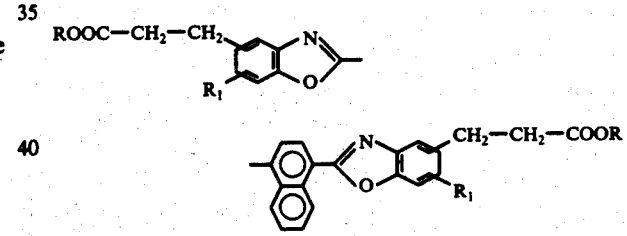

wherein
R and $R_1$ represent a lower alkyl radical which may be branched, or a hydrogen atom.

* * * * *